(12) United States Patent
Lawless

(10) Patent No.: US 6,824,661 B2
(45) Date of Patent: Nov. 30, 2004

(54) COMBINED OXYGEN AND $NO_X$ SENSOR

(75) Inventor: William N. Lawless, Westerville, OH (US)

(73) Assignee: CeramPhysics, Inc., Westerville, OH (US)

( * ) Notice: Subject to any disclaimer, the term of this patent is extended or adjusted under 35 U.S.C. 154(b) by 370 days.

(21) Appl. No.: 10/010,231

(22) Filed: Dec. 7, 2001

(65) Prior Publication Data

US 2002/0046947 A1 Apr. 25, 2002

Related U.S. Application Data

(63) Continuation-in-part of application No. 09/662,773, filed on Sep. 15, 2000.
(60) Provisional application No. 60/254,081, filed on Dec. 7, 2000, and provisional application No. 60/155,817, filed on Sep. 23, 1999.

(51) Int. Cl.[7] ............................................. G01N 27/407
(52) U.S. Cl. ...................... 204/426; 204/425; 73/23.31; 205/781
(58) Field of Search ................................ 204/424, 425, 204/426; 205/784, 785, 781; 73/23.31, 23.32

(56) References Cited

U.S. PATENT DOCUMENTS

| | | |
|---|---|---|
| 3,400,054 A | 9/1968 | Ruka et al. |
| 3,768,259 A | 10/1973 | Carnahan et al. |
| 3,819,500 A | 6/1974 | Van Esdonk et al. |
| 3,859,192 A | 1/1975 | Barnes et al. |
| 3,871,981 A | 3/1975 | Flais et al. |
| 3,909,385 A | 9/1975 | Spielberg et al. |
| 3,948,813 A | 4/1976 | Holcombe, Jr. et al. |
| 3,974,054 A | 8/1976 | Poolman et al. |
| 4,021,326 A | 5/1977 | Pollner et al. |
| 4,195,119 A | 3/1980 | Kummer |
| 4,207,159 A | 6/1980 | Kimura et al. |
| 4,208,265 A | 6/1980 | Hori et al. |
| 4,218,297 A | 8/1980 | Henault et al. |
| 4,231,231 A | 11/1980 | Lawless |
| 4,296,147 A | 10/1981 | Lawless |
| 4,296,607 A | 10/1981 | Lawless |
| 4,296,608 A | 10/1981 | Lawless |
| 4,354,355 A | 10/1982 | Lawless |
| 4,356,235 A | 10/1982 | Lawless |
| 4,396,721 A | 8/1983 | Lawless |
| 4,449,990 A | 5/1984 | Tedford, Jr. |
| 4,462,891 A | 7/1984 | Lawless |

(List continued on next page.)

FOREIGN PATENT DOCUMENTS

| | | |
|---|---|---|
| EP | 0 726 226 A1 | 8/1996 |
| EP | 0 778 069 A1 | 6/1997 |
| GB | 2 288 873 A  * | 1/1995 |
| WO | WO 95/08360 | 3/1995 |

* cited by examiner

Primary Examiner—Kaj K. Olsen
(74) Attorney, Agent, or Firm—Dinsmore & Shohl LLP

(57) ABSTRACT

A combined oxygen and $NO_x$ sensor is provided. Generally, the combined sensor employs a sensor body that includes two different types of electrodes—oxygen-porous electrode layers and dissociative oxygen-porous electrode layers. In accordance with one embodiment of the present invention, the sensor comprises a sensor body, an oxygen content electrical signal output, and a $NO_x$ content electrical signal output. The sensor body is disposed in the gas and comprises a plurality of oxygen-porous electrode layers and a plurality of dissociative oxygen-porous electrode layers. The dissociative oxygen-porous electrode layers comprise a material selected to catalyze dissociation of $NO_x$ into nitrogen and oxygen.

28 Claims, 6 Drawing Sheets

| | | | | | | |
|---|---|---|---|---|---|---|
| 4,464,244 A | 8/1984 | Uchida et al. | | 5,736,028 A | 4/1998 | Hjortsberg et al. |
| 4,502,939 A | 3/1985 | Holfelder et al. | | 5,807,642 A | 9/1998 | Xue et al. |
| 4,515,534 A | 5/1985 | Lawless et al. | | 5,855,762 A | 1/1999 | Phillips et al. |
| 4,541,899 A | 9/1985 | Mase et al. | | 5,865,877 A | 2/1999 | Delp, II |
| 4,545,254 A | 10/1985 | Lawless et al. | | 5,905,000 A | 5/1999 | Yadav et al. |
| 4,547,277 A | 10/1985 | Lawless | | 5,922,178 A | 7/1999 | Isenberg |
| 4,547,281 A | 10/1985 | Wang et al. | | 6,068,747 A * | 5/2000 | Tojo et al. .................. 204/425 |
| 4,599,677 A | 7/1986 | Lawless et al. | | | | |
| 4,642,174 A | 2/1987 | Shibata | | | | |
| 4,684,207 A | 8/1987 | Lawless | | | | |
| 4,789,388 A | 12/1988 | Nishibata et al. | | | | |
| 4,885,142 A | 12/1989 | Suitor et al. | | | | |
| 4,918,421 A | 4/1990 | Lawless et al. | | | | |
| 5,009,763 A | 4/1991 | Hise | | | | |
| 5,034,023 A | 7/1991 | Thompson | | | | |
| 5,062,911 A | 11/1991 | Hampton et al. | | | | |
| 5,108,465 A | 4/1992 | Bauer et al. | | | | |
| 5,169,506 A | 12/1992 | Michaels | | | | |
| 5,183,965 A | 2/1993 | Lawless | | | | |
| 5,186,793 A | 2/1993 | Michaels | | | | |
| 5,205,990 A | 4/1993 | Lawless | | | | |
| 5,212,013 A | 5/1993 | Gupta et al. | | | | |
| 5,222,713 A | 6/1993 | Lawless et al. | | | | |
| 5,246,729 A | 9/1993 | Gupta et al. | | | | |
| 5,296,110 A | 3/1994 | Tabatabaie-Raissi | | | | |
| 5,302,258 A | 4/1994 | Renlund et al. | | | | |
| 5,385,874 A | 1/1995 | Renlund et al. | | | | |
| 5,393,399 A | 2/1995 | Van den Berg et al. | | | | |
| 5,397,443 A | 3/1995 | Michaels | | | | |
| 5,441,610 A | 8/1995 | Renlund et al. | | | | |
| 5,536,378 A | 7/1996 | Gibson et al. | | | | |
| 5,549,983 A | 8/1996 | Yamanis | | | | |
| 5,589,017 A | 12/1996 | Minh | | | | |
| 5,611,845 A | 3/1997 | Delp, II | | | | |
| 5,643,355 A | 7/1997 | Phillips et al. | | | | |
| 5,672,811 A | 9/1997 | Kato et al. | | | | |
| 5,712,055 A | 1/1998 | Khandkar et al. | | | | |
| 5,731,097 A | 3/1998 | Miyashita et al. | | | | |

COMBINED OXYGEN AND NO$_x$ SENSOR

CROSS-REFERENCE TO RELATED APPLICATIONS

This application claims the benefit of U.S. Provisional Application Ser. No. 60/254,081, filed Dec. 7, 2000. This application is also a continuation-in-part of U.S. patent application Ser. No. 09/662,773, filed Sep. 15, 2000, which claims the benefit of U.S. Provisional Application Ser. No. 60/155,817, filed Sep. 23, 1999.

BACKGROUND OF THE INVENTION

The present invention relates to a device for sensing the partial pressure of oxygen in a gas, and more particularly to an active multilayer sensor utilizing an oxygen ion conducting material. The present invention also relates to a combined sensor for measuring oxygen content and NO$_x$ content in a gas. NO$_x$ is utilized herein to represent nitric oxide, nitrogen dioxide, nitrogen trioxide, etc.

It is widely recognized that one of the most important diagnostics for monitoring the efficiency of any combustion process is the measurement of the oxygen partial pressure in an exhaust gas. Thus, oxygen sensors have long been used to measure the oxygen content of exhaust gases from such diverse combustion processes as internal combustion engines in motor vehicles and coal, natural gas, or oil burning power generation facilities.

The most widely known and used oxygen sensors are based on partially stabilized zirconia (PSZ) as the ion conductor. Such sensors function by monitoring the electromotive force (EMF) developed across an ion conductor which is exposed to different partial pressures of oxygen. Oxygen tends to move from a gas containing a high concentration of oxygen to one of lower concentration. If two gases are separated from each other by an electroded oxygen ion conductor, the oxygen molecules will dissociate on one surface of the conductor and absorb electrons to form oxygen ions. These ions then diffuse through the ionic conductor, leaving the entry surface with a deficiency of electrons ($O_2+4e=2O^{-2}$). On the exit or low oxygen concentration side of the conductor, oxygen ions leaving the conductor must give up electrons to form molecular oxygen, thus leaving the exit surface with an excess of electrons. This creates the EMF between the two surfaces of the ion conductor.

One problem with the use of partially stabilized zirconia sensors is that they must be operated at temperatures in the range of about 800 C. to reduce internal resistance to a point where a current can be measured. Further, the raw material costs of stabilized zirconia is relatively high, and the melting point of zirconia is quite high (2700 C.) so that formation of sensors is expensive.

Lawless, in U.S. Pat. No. 4,462,891, describes a passive oxygen sensor using ceramic ion conducting materials based on nickel niobates and Bismuth oxides. The oxygen sensor includes a plurality of layers of the ceramic material and a porous metallic conductor arranged to form a body having alternating ceramic and metallic layers, with first alternate ones of the metallic layers being exposed along one side of the body and second alternate ones of the metallic layers being exposed along an opposite side of the body. The first and second alternate ones of the metallic layers are exposed to separate gases, one of the gases being a reference gas, in order to create a voltage output signal across electrodes connected to alternate metallic layers. The voltage output signal is indicative of the relative oxygen partial pressures of the separate gases. Thus, the passive oxygen sensor cannot provide an oxygen partial pressure indication unless the first and second metallic layers present in the body are exposed, respectively, to a sample gas and a separate reference gas having a known oxygen partial pressure, i.e., each side of the sensor body must be exposed to a separate gas.

More recently, amperometric sensors have been introduced which also use partially stabilized zirconia but which do not require a reference gas to operate. Such a sensor 80 is illustrated in FIG. 1 and comprises a cavity 100 in communication with the unknown gas through a diffusion hole 120. The base of the cavity 100 is a PSZ electrolyte 140 which is connected through electrodes 160, 160' to a voltage source 170. The application of a voltage causes oxygen to be pumped from the cavity through diffusion into the surrounding gas as shown by the arrows. If the cavity is sealed atop the base, and if the top of the cavity has the small diffusion hole 120, then a point is reached on increasing the voltage where no more oxygen can be pumped out of the cavity than is entering through the diffusion hole. The current drawn at this point is called the amperometric current. The larger the oxygen partial pressure in the surrounding gas, the larger will be the amperometric current. Thus, a measurement of the amperometric current yields the oxygen partial pressure. Again, however, this sensor suffers from some of the same drawbacks in that materials and fabrication costs are relatively high. An extremely small diffusion hole is required, about 5 $\mu$m, and requires precise machining because the size is critical to the operation of the sensor. Additionally, the manufacture of the sensor of FIG. 1 requires five silk screen operations and four burnout steps. Finally, these sensors lose their sensitivity above about 80% oxygen and the diffusion hole is prone to plugging.

Accordingly, there remains a need in the art for an amperometric oxygen sensor which is relatively inexpensive to manufacture and provides enhanced oxygen sensitivity. There is also a need in the art for a sensor which is capable of providing an independent indication of NO$_x$ content in a gas.

BRIEF SUMMARY OF THE INVENTION

These needs are met by the present invention wherein a combined oxygen and NO$_x$ sensor is provided. Generally, the combined sensor employs a sensor body that includes two different types of electrodes—oxygen-porous electrode layers and dissociative oxygen-porous electrode layers.

In accordance with one embodiment of the present invention, a combined sensor for measuring oxygen content and NO$_x$ content in a gas is provided. The sensor comprises a sensor body, an oxygen content electrical signal output, and a NO$_x$ content electrical signal output. The sensor body is disposed in the gas and comprises (i) a plurality of oxygen-porous electrode layers, (ii) a plurality of dissociative oxygen-porous electrode layers, wherein the dissociative oxygen-porous electrode layers comprise a material selected to catalyze dissociation of NO$_x$ into nitrogen and oxygen, and (iii) a plurality of oxygen ion conductive ceramic layers interposed between respective ones of the oxygen-porous electrode layers and respective ones of the dissociative oxygen-porous electrode layers. The oxygen content electrical signal output is coupled to the plurality of oxygen-porous electrode layers. Similarly, the NO$_x$ content electrical signal output is coupled to the plurality of dissociative oxygen-porous electrode layers. The NO$_x$ content electrical signal output is electrically isolated from the oxygen content electrical signal output.

In accordance with another embodiment of the present invention, a combined sensor for measuring oxygen content and $NO_x$ content in a gas is provided where the dissociative oxygen-porous electrode layers comprise sufficient Rh to catalyze dissociation of $NO_x$ into nitrogen and oxygen. In accordance with yet another embodiment of the present invention, a combined sensor for measuring oxygen content and $NO_x$ content in a gas is provided. The sensor comprises a partial enclosure defining a gas passage, a sensor body, and a diffusion barrier. The diffusion barrier defines a diffusion-limited portion of the gas passage and the sensor body is disposed in the diffusion-limited portion of the gas passage.

In accordance with yet another embodiment of the present invention, a sensor body is provided comprising a plurality of oxygen-porous electrode layers, a plurality of dissociative oxygen-porous electrode layers, and a plurality of oxygen ion conductive ceramic layers. The dissociative oxygen-porous electrode layers comprise a material selected to catalyze dissociation of $NO_x$ into nitrogen and oxygen. The plurality of oxygen ion conductive ceramic layers are interposed between respective ones of the oxygen-porous electrode layers and respective ones of the dissociative oxygen-porous electrode layers.

Accordingly, it is an object of the present invention to provide an improved oxygen and $NO_x$ sensing device. Other objects of the present invention will be apparent in light of the description of the invention embodied herein.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which.

DETAILED DESCRIPTION

The present invention is described herein with initial reference to an amperometric oxygen sensor and with subsequent reference to a combined oxygen and $NO_x$ sensor that utilizes an oxygen sensor and additional structure similar to the basic oxygen sensor structure.

Amperometric Oxygen Sensor

Figure 1:
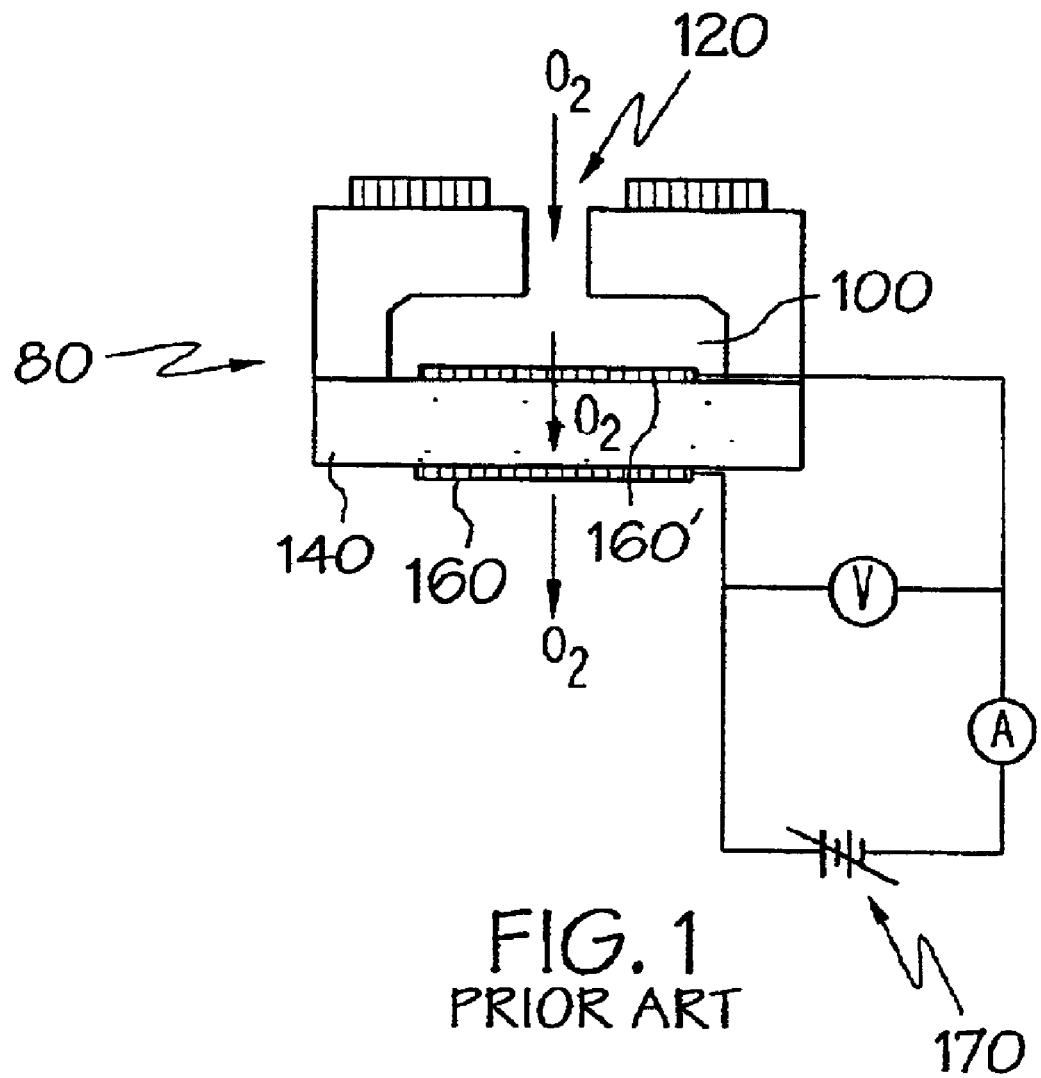
FIG. 1 is a schematic representation of a prior art oxygen sensor.
Figure 2:
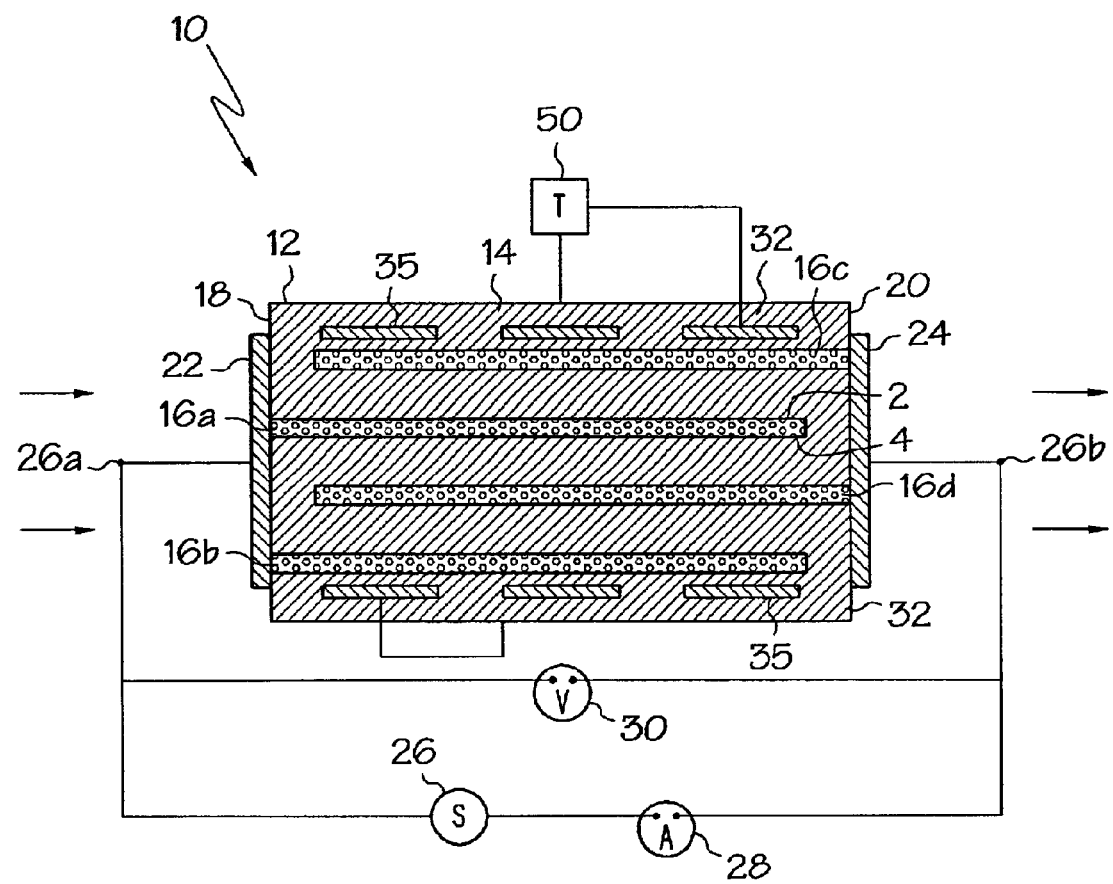
FIG. 2 is a schematic representation of an oxygen sensor in accordance with the present invention.

A schematic representation of an amperometric oxygen sensor constructed according to the present invention is shown in FIG. 2. As seen in FIG. 2, oxygen sensor 10 includes a sensor body 12 having alternating layers of an oxygen ion conducting material 14 and an oxygen-porous electrically conductive material 16a, 16b, 16c, 16d. A first set of oxygen-porous conductive layers 16a and 16b have end portions that are exposed along a first edge 18 of the sensor body 12. For the purpose of describing and defining the present invention, an oxygen ion conductor is any material capable of achieving electrical conductivity due to displacement of oxygen ions within its crystal lattice.

Electrical connections are made to the conductive layers 16a and 16b by firing electrically conductive oxygen-porous terminations 22 onto the ends of the conductive layers 16a, 16b to form a plurality of cathode layers. A second set of oxygen-porous conductive layers 16c and 16d have end portions that are exposed along a second edge 20 of the sensor body 12. The conductive layers 16c and 16d are electrically connected to one another by an electrically conductive oxygen-porous termination 24, to form a plurality of anode layers. Silver or oxygen-porous platinum are suitable materials for use as the electrically conductive oxygen-porous terminations 22, 24. The terminations 22, 24 are used to electrically connect the ceramic layers in parallel to reduce the electrical resistance of the sensor and allow increased amperometric current.

Each of the conductive layers 16a–16d includes two major surfaces. For example, conductive layer 16a includes major surfaces 2 and 4. Each oxygen ion conductor layer 14 is disposed between major surfaces of opposing conductive layers. Further, both major surfaces of each conductive layer are unexposed, i.e., enclosed by the sensor body 12. It is contemplated by the present invention that any number of oxygen-porous conductive layers and ion conductor layers may be used to construct the sensor body 12. The number of layers shown in FIG. 2 is merely presented for illustrative purposes.

A voltage source 26 is electrically connected to the terminations 22 and 24. In this manner, a first pole 26a of the voltage source 26 is electrically connected to the cathode layers formed by conductive layers 16a and 16b and a second pole 26b of the voltage source 26 is electrically connected to the anode layers formed by conductive layers 16c and 16d. An amperometric current meter 28 is connected between the voltage source 26 and the termination 24. A voltage meter 30 is connected across the voltage source 26.

The oxygen-porous electrically conductive material forming conductive layers 16a–d preferably comprises oxygen-porous platinum, although any suitable electrically conductive material which is porous to oxygen and catalyzes oxygen molecules to ions at the cathode layers and catalyzes ions to oxygen molecules at the anode layers may be used.

Platinum electrodes can be made porous to oxygen by well-known methods. For example, the use of coarse Pt particles in electroding ink results in porous electrodes. Other additions to the electroding ink, such as zirconia particles, further increase the porosity. A platinum electrode having 5–30% of its volume occupied by pores is one preferred example. As another example, 85 parts, by weight, of a coarse Pt powder available as platinum powder number 6432\0101 from Demetron, GMBH, Hanau, Germany, may be combined with 15 parts, by weight, of a 400 mesh zirconia powder in a suitable silk screening slurry.

In one embodiment of the present invention, the width of the sensor body 12, i.e., the dimension of the sensor body from the first edge 18 to the second edge 20, is about 0.20" (0.5 cm), the short ends of the conductive layers 16a, 16b, 16c, 16d terminate about 0.030" (0.075 cm) from respective side edges, leaving a 0.14" (0.36 cm) conductive layer overlap. The length of the sensor body 12 is about 0.18" (0.46 cm). The thickness of the sensor body 12 is defined by the number and thickness of the oxygen ion conductor layers 14, the conductive layers 16a, 16b, 16c, 16d, and any layers dedicated to a heating circuit (described below). In one embodiment of the present invention, eleven oxygen ion conductor layers 14 are positioned between alternate ones of twelve conductive layers 16a, 16b, 16c, 16d. The oxygen ion conductor layers 14 may comprise 0.0030" (0.076 mm) thick yttria-stabilized zirconia layers. The conductive layers comprise 0.0001" (0.0025 mm) thick porous platinum. The result is an oxygen sensor that is relatively compact in size and relatively inexpensive to produce.

A number of ceramic oxygen ion conductor materials may be used in accordance with the present Invention. Indeed, the present invention's advantages of simplicity of construction and reduced electrical resistance due to sensor geometry are applicable to any of a wide variety of ceramic materials used. Preferably, the oxygen ion conductor of the present invention is a ceramic electrolyte and more specifically, comprises yttria-stabilized zirconia ($ZrO_2$ stabilized with $Y_2O_3$) but may also comprise stabilized bismuth oxide, stabilized ceria, etc. The zirconia ceramic may be stabilized with materials other than $Y_2O_3$.

Fine grain sized powders of $ZrO_2:Y_2O_3$ can be sintered to high density at 1150–1300 C., making it possible to manufacture multi-layer sensor bodies from this oxygen ion conductor.

Because of the convenient sintering temperatures of the ceramic materials of the present invention, the ceramics can be "tape cast" into a monolithic body. As is well known in the ceramic art, tape casting is a process for making a multilayered body (for example, a ceramic capacitor) wherein appropriate metal electrodes are interdispersed between the ceramic layers. A tape casting technique may be employed such as that described in U.S. Pat. No. 4,462,891, incorporated herein by reference. The ceramic layers are quite thin, having a thickness of from about 25–100 $\mu$m. Further, this tape casting method requires only a single silk screening operation and a single burnout step.

Higher porosity levels in the conductive layers are more suitable for sensing very low levels of oxygen in a gas, e.g., as low as 1 ppm oxygen partial pressure. Conversely, lower porosity levels in the conductive layers are more suitable for sensing applications over a broad range of oxygen partial pressure up to a maximum of $10^6$ ppm. According to one embodiment of the present invention, the amperometric oxygen sensor 10 is produced by sintering the entire sensor body 12, i.e., the oxygen ion conductor layers 14, the conductive layers 16a, 16b, 16c, 16d, and any layers dedicated to the heating circuit 12, at a sintering temperature selected to yield a predetermined oxygen porosity in the conductive layers 16a, 16b, 16c, 16d. Sintering at relatively high temperatures for relatively large amounts of time decreases the porosity in the electrode layers because the density of the sensor body increases. Conversely, sintering at relatively low temperatures for relatively short amounts of time does not lead to equally significant decreases in porosity in the electrode layers because the density of the sensor body does not increase as much as is the case for higher temperature and longer duration sintering.

Accordingly, an amperometric oxygen sensor according to the present invention may be produced by providing an unsintered sensor body, selecting a target porosity for the oxygen-porous electrode layers, and selecting a corresponding sintering temperature for the sensor body. The sintering temperature is selected to correspond to the target porosity and may be determined through experimentation. The sensor body is sintered at the selected sintering temperature to yield a sintered sensor body including oxygen porous electrode layers having a target porosity. For example, where the conductive layers are sintered at about 1200° C., for a duration of about 2 hours, the sintered sensor body is suitable for oxygen sensing in gases having an oxygen content ranging from a value typically found in air to values as low as 1 ppm or lower. If the sensor body is sintered at a higher temperature, e.g., 1275° C., for the same duration, a less porous layer is formed and the sintered sensor body is more suitable for oxygen sensing of gases having higher oxygen concentrations, e.g., up to 100% oxygen.

There may be some increase in resistance in the oxygen porous electrode layers over time as a result of sintering of platinum particles in the electrodes at the operating temperature of the sensor. The long term stability of sensors according to the present invention may be improved in some instances by stabilizing the oxygen porous electrode layers against sintering. It should be appreciated by those practicing the present invention that a variety of methods are available for stabilizing platinum electrodes against sintering.

In operation, the oxygen sensor 10 is immersed in a gas whose oxygen partial pressure is to be determined. If there is not already oxygen present in the porous conductive layers 16a–d, oxygen from the gas passes through the porous terminations 22 and 24 and enters the porous electrodes 16a–d through diffusion. A voltage from voltage source 26 is applied across the terminations 22 and 24. The resulting voltage difference between the conductive layers 16a and 16b, also referred to herein as the cathode layers, and the conductive layers 16c and 16d, also referred to herein as the anode layers, will cause oxygen to be pumped through the layers of oxygen ion conducting material 14. Since the porous electrode layers 16a–d catalyze oxygen molecules to ions at the cathode layers 16a, 16b and catalyze ions to oxygen molecules at the anode layers 16c, 16d, oxygen enters at the cathode layers 16a, 16b, is pumped through the layers of ion conductor material 14, and exits through the anode layers 16c, 16d. The resulting electrical current is measured by the amperometric meter 28 and is indicative of the oxygen partial pressure of the gas.

Sensors based on stabilized zirconia tend to have operating temperatures above 700° C. The applied voltage is monitored by the voltage meter 30. It has been found that applied dc voltages at and above 0.2 volts often lead to instabilities in the sensor and that an applied voltage of 0.05 volts has been found to yield unstable current signals at large oxygen partial pressures.

An applied voltage of 0.1 volts is the preferred bias voltage. The voltage source may be a dc voltage source or an ac voltage source operating at about 3 Hz. The preferred ac frequency is less than 50 Hz since, as the ac frequency increases, the sensor response to oxygen decreases. Because the oxygen sensor of the present invention operates at an elevated temperature, it is preferable to provide a heater and thermometer for the sensor body.

Figure 3:
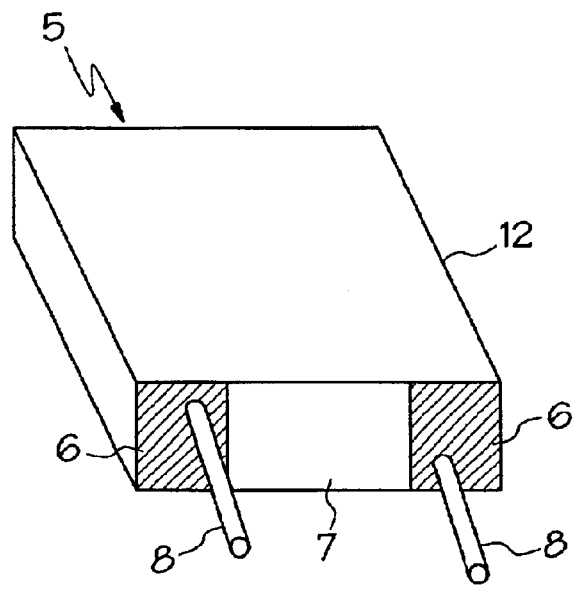
FIGS. 3–5 are illustrations of an alternative heating circuit arrangement according to the present invention.
Figures 4, 5:
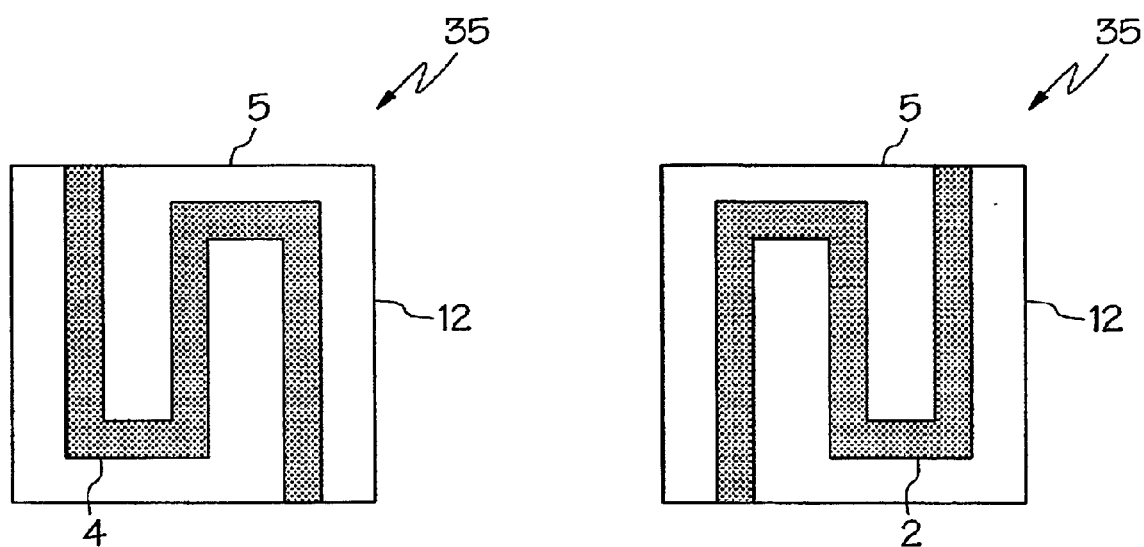

Resistive heating electrodes 35 are provided in the manner illustrated in FIGS. 2–5. As is illustrated in FIGS. 2–5, cover plate heating electrodes 35 in the form of platinum tracks are embedded in the ion conductor material 14 of the sensor body 12, more specifically in the top and bottom cover plates 32. Referring specifically to FIGS. 3-5, the sensor body 12 is provided with a top heater track 2 and a bottom heater track 4. The rear face 5 of the sensor body 12 is provided with a conductive termination arranged to couple conductively the top heater track 2 to the bottom heater track 4. In addition, the front face 7 of the sensor body 12 is provided with a pair of conductive terminations 6 coupled conductively to respective ones of the top heater track 2 and the bottom heater track 4. In this manner, a complete circuit is formed by coupling a heating voltage source (incorporated in heating circuit controller 50) and terminals 8 to respective ones of the conductive terminations 6.

The measured resistance in the embedded platinum heater track 35 typically varies from about 2.3 to about 6.5 ohms between 25° C. and 800° C., respectively. The measured heater power required to maintain the sensor body 12 ranges up to about 2 watts at 800° C., a preferred sensor operating temperature. A heating voltage is applied across the heating circuit by connecting a heating voltage source across the heating electrodes 35. The resistivity of the heating circuit generates heat when a voltage is applied. The resistance of the heating electrodes 35 varies as a function of temperature. This temperature/resistance relation provides a means for measuring the temperature of the sensor body 12. Preferably, the heating electrodes 35 are coupled to a heating circuit controller 50 programmed to control the resistance of the heating electrodes 35 by applying a constant current to the heating electrodes 35 and controlling the voltage applied thereto.

As is illustrated in FIGS. 2–5, top and bottom dielectric cover plates 32 preferably comprise a 0.02" (0.05 cm) thick dielectric material added above and below the uppermost and lowermost electroded layers of the sensor body 12 for electrical insulation and structural integrity. The sensor body 12 may be incorporated into a four pin package, two connections for the heating circuit, a cathode connection, and an anode connection, surrounded by thermal insulation, and enclosed by a Teflon particulate filter.

Conductive Au or Pt leads may be coupled to the various sensor electrodes by attaching the leads to the exposed electrode portions on the sensor body 12 with an Au or Pt paste.

Alternatively, sensor packaging can be simplified by embedding the conductive leads in the sensor body 12. Specifically, small holes (~0.6 mm) may be drilled in the sensor body 12 prior to sintering and Pt or Au wires may be inserted, with a suitable conductive paste, into the holes.

A preferred heating control scheme involves applying the constant current to the heater electrodes 35 in square-wave pulses and using the voltage signal to control the pulse width of the current pulses (pulse-width modulation). Under feedback control the pulse width is modulated to maintain the voltage constant, thereby maintaining the resistance of the heating electrodes 35 constant, as desired. Stated differently, modulating the pulse width of the current controls the heating power applied to the heating electrodes 35 to maintain the sensor temperature constant. The voltage can easily be read using a 16 bit A/D converter to an accuracy of ±0.0015%. Conventional current control schemes allow maintenance of a constant current within about 0.01%. Therefore, the temperature of the integrated sensor body can be controlled within acceptable ranges.

A preferred microprocessor-based heating circuit controller 50 consists of a temperature-control section and a sensor-output section. The latter section would supply a constant voltage to the heating electrodes 35 and read the amperometric current in the heating electrodes 35. The current signal may be converted to a readout of the oxygen partial pressure and may be converted to an output suitable for controlling a combustion process.

The sensor 10 may be calibrated and used by first identifying the resistance of the heating electrodes 35 in the desired operating temperature range. This resistance value, e.g. 9–10 ohms at 600 C., is known and typically is well defined within a given temperature range. Corresponding current and voltage parameters, e.g., 0.47 A and 4.1 volts, are programmed into the heating circuit controller 50, and the controller 50 is programmed to maintain these values. The actual operating temperature of any individual sensor is held constant within the sensor's operating range.

As an illustrative example, where 1 mil=0.001 inches= 0.0254 mm, a preferred sensor body is 166 mil×124 mil×53 mil (4.22 mm×3.15 mm×1.35 mm) and weighs 144 mg. In the embodiment of the present invention where cover plate heating electrodes 35 are employed, the total electrode overlap area per layer is preferably about 12.7 mm2 and the total area to thickness ratio of the oxygen sensor body 12 is about 199 cm. The exposed edge of each electrode is 50 mil (1.27 mm) wide, and each electrode extends 153 mil (3.89 mm) into the body. The resistive heating electrodes are preferably porous Pt tracks approximately 166 mil (4.22 mm) in length and 22 mil (0.559 mm) in width, whereby a heater current of 223 mA is typical for a control temperature of about 600° C.

Figure 6A:
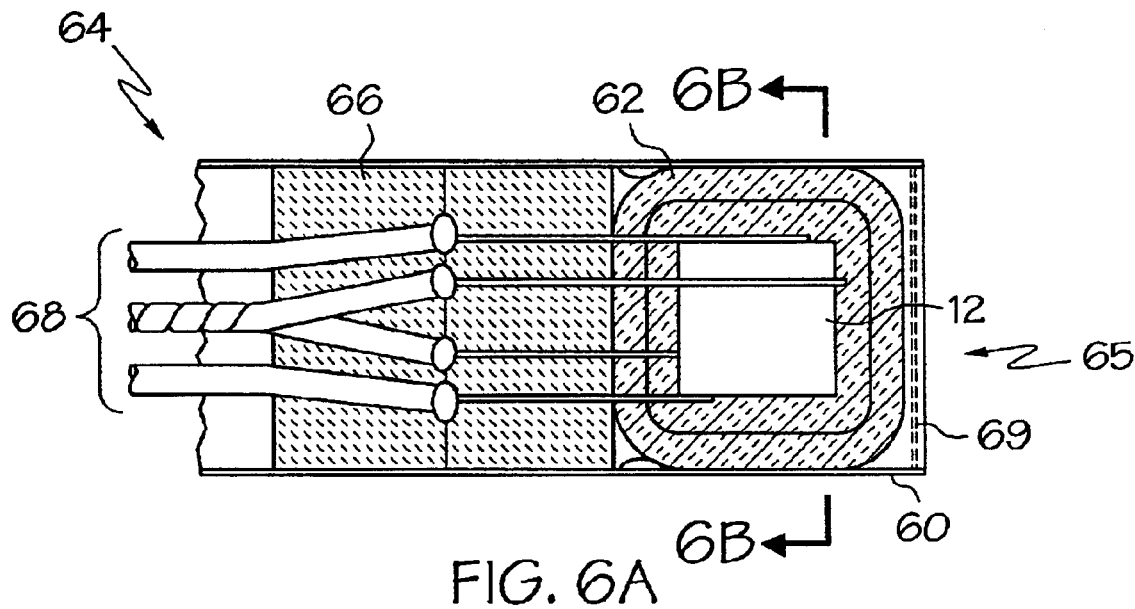
FIGS. 6A and 6B are illustrations of a packaging scheme according to one embodiment of the present invention.
Figure 6B:
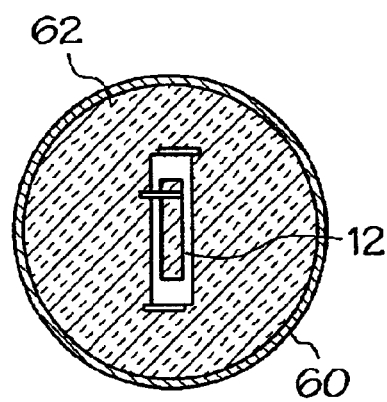
Figure 7:
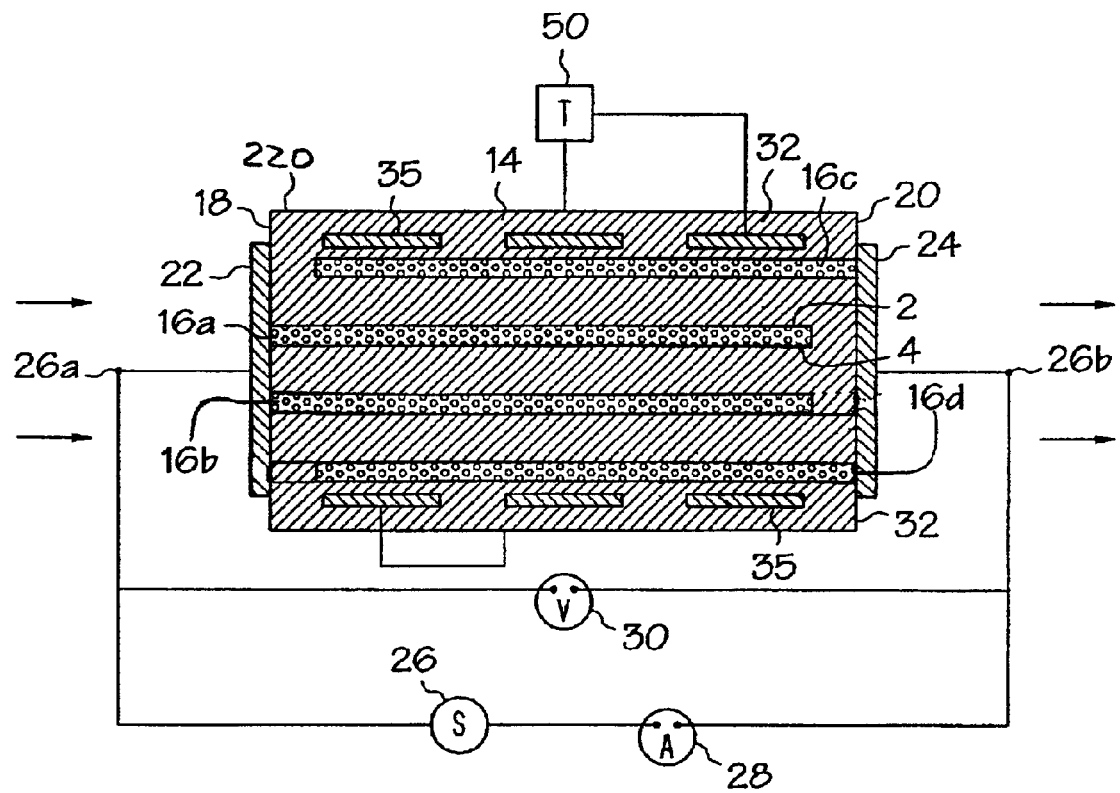
FIG. 7 is an illustration of a sensor body for use in a combined sensor for measuring oxygen content and $NO_x$ content in a gas.
Figures 8A, 8B, 8C:
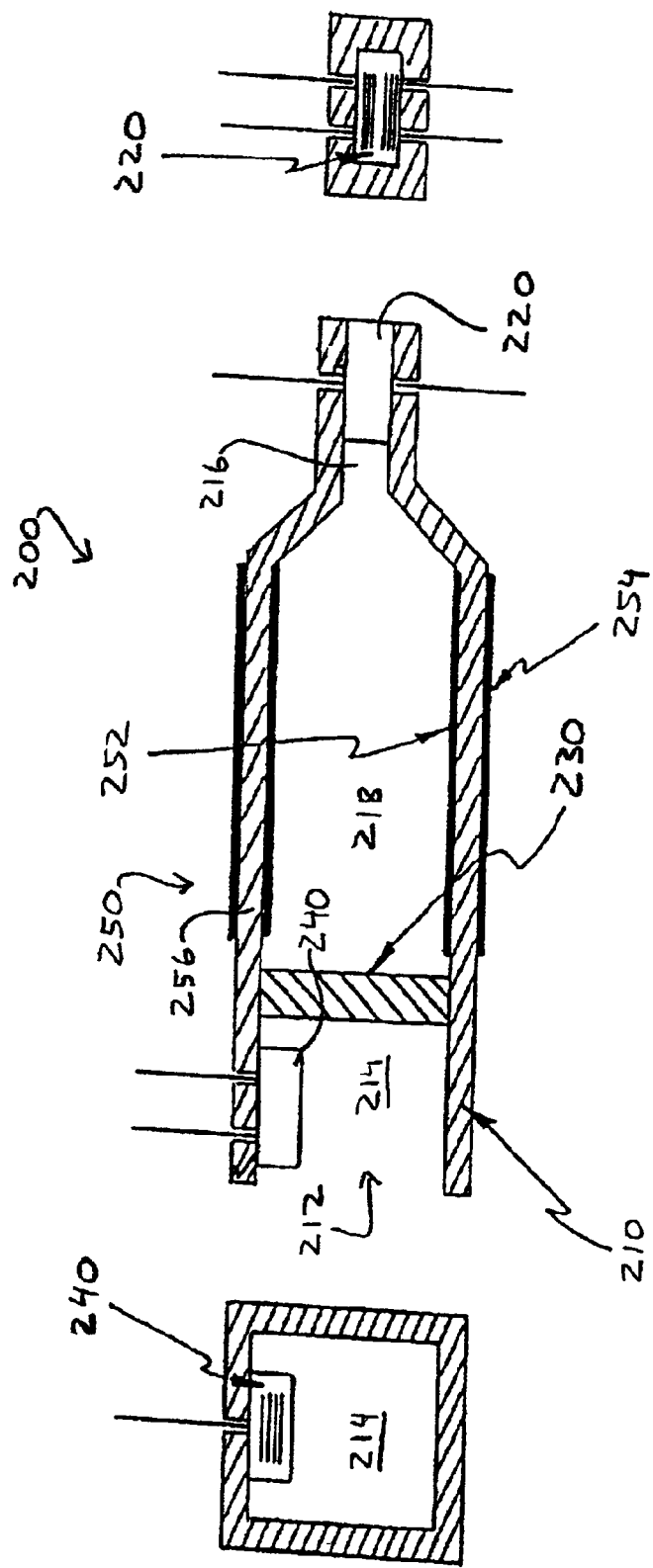
FIGS. 8A–8C illustrate a combined sensor for measuring oxygen content and $NO_x$ content in a gas.

Referring now to FIGS. 6A and 6B, a packaging scheme according to one embodiment of the present invention is illustrated. In the illustrated embodiment, the sensor body 12 is enclosed in a stainless steel tube 60. The thickness of the tube 60 is preferably selected to be machinable for threads for mounting the package into a bulkhead or exhaust flue. The sensor body 12 is stabilized and thermally insulated within the tube 60 by means of suitable gas permeable thermal insulation 62 (e.g., Nextel 312 thermal insulation). A back end 64 of the tube 60 is sealed with a ceramic 66. Electrical connections 68 to the sensor body 12 are potted in the ceramic 66 and routed through the insulation 62. Preferably, the electrical connections comprise 20 gauge copper leads coupled to the four sensor leads. A front end 65 of the tube 60 is provided with a stainless steel screen 69 to permit gas to reach the sensor body 12.

While certain representative embodiments and details have been shown for purposes of illustrating the invention, it will be apparent to those skilled in the art that various changes in the methods and apparatus disclosed herein may be made without departing from the scope of the invention, which is defined in the appended claims. For example, although the sensor 10 of the present invention is well suited for measuring excess oxygen partial pressure because the oxygen-porous terminations 22, 24 present a catalysis area for the combustion of CO and other combustibles, it is noted that the present invention may be arranged for measuring actual oxygen partial pressure rather than excess oxygen partial pressure. Specifically, the cathode electrodes 16a, 16b exposed on the first edge 18 of the sensor body 12 are very thin and present a very small catalysis area for the combustion of CO and other combustibles. Accordingly, by omitting the oxygen-porous terminations 22, 24, the sensor 10 of the present invention may be arranged for measuring actual oxygen partial pressure rather than excess oxygen partial pressure.

Further, it is contemplated by the present invention that a pair of sensors could be packaged to yield both actual and excess oxygen measurements simply by providing the oxygen-porous terminations 22, 24 on one sensor body only. Finally, it is noted that an alternate method of measuring actual and excess oxygen using two sensors would be to maintain one sensor below the ignition temperature of CO (600–650° C.) and the second sensor above this temperature, also in a single package.

Combined Oxygen and $NO_x$ Sensor

Referring now to FIGS. 7 and 8A–8C, a combined sensor 200 for measuring oxygen content and $NO_x$ content in a gas is described. The sensor 200 comprises a partial enclosure 210, a sensor body 220 disposed in the partial enclosure 210, a diffusion barrier 230, and an oxygen sensor 240. As will be described in further detail below, the sensor body 220 is configured to provide an indication of the $NO_x$ content of the gas and the oxygen sensor 240 is configured to provide an indication of the oxygen content of the gas. The sensor 200 includes many components identical or similar in structure to those described in detail above with reference to FIG. 2. Like reference numerals are utilized in FIGS. 2 and 7 corresponding to the like elements and reference is made to the discussion of FIG. 2 for a description of these elements.

The partial enclosure 210 defines a gas passage 212 and is referred to herein as "partial" because it encloses a defined space but also defines the gas passage 212, an inlet portion 214, and an outlet portion 216. The partial enclosure 210 typically comprises an oxygen-ion conductive ceramic tube. It is noted that, although the enclosure is illustrated with a rectangular cross-section, an enclosure with a circular cross section is likely to be more effective and easier to manufacture.

The diffusion barrier 230 extends across the gas passage 212 and defines a diffusion-limited portion 218 of the gas passage 212 between the inlet portion 214 and the outlet portion 216. The enclosure 210, the diffusion barrier 230, and the sensor body 220 are configured such that the diffusion-limited portion 218 of the gas passage 212 comprises a hermetically sealed zone including a diffusion inlet defined by the diffusion barrier 230 and a sensor outlet defined by the sensor body 220. An oxygen pumping portion 250, described in detail below, is also provided in the hermetically sealed zone.

The diffusion barrier 230 is porous to oxygen and $NO_x$ and may comprise, for example, a substantially uniform zirconia partition. Typically, the diffusion barrier is configured to pass an amount of gas that varies as a function of oxygen partial pressure of gas within an inlet portion of the gas passage. It is contemplated that the diffusion barrier may define a variety of configurations including, for example, a perforated plate, a plate including a single restricted aperture, etc.

The sensor body 220 extends across the outlet portion 216 of the gas passage 212 and is disposed in the diffusion-limited portion 218 of the gas passage 212. The sensor body 220 differs from the sensor body 12 illustrated in FIG. 2 in that selected ones of the oxygen porous conductive layers are formed from a material that catalyzes the dissociation of $NO_x$ into $N_2$ and $O_2$. In this manner, dissociated $O_2$ may be measured as an amperometric current and the amperometric current may be related to $NO_x$ content. The conductive layers that do not catalyze the dissociation of $NO_x$ into $N_2$ and $O_2$, i.e., the non-dissociative electrode layers, are utilized to provide an indication of oxygen content, as will be described in further detail herein.

Specifically, the sensor body 220 comprises a plurality of oxygen-porous electrode layers 16a, 16c and a plurality of dissociative oxygen-porous electrode layers 16b, 16d. As is described above with reference to the oxygen sensor of FIG. 2, the oxygen-porous electrode layers 16a, 16c catalyze cause oxygen to be pumped through the layers of oxygen ion conducting material 14 by catalyzing oxygen molecules to ions at the cathode layers and catalyzing ions to oxygen molecules at the anode layers. The resulting electrical current is measured by the amperometric meter 28 and is indicative of the oxygen partial pressure of the gas. The dissociative oxygen-porous electrode layers 16b, 16d pump oxygen through this process as well but additionally pump oxygen dissociated from $NO_x$ in the gas by catalyzing the dissociation of $NO_x$ into $N_2$ and $O_2$ at the cathode layers. As a result, the resulting electrical current at the dissociative oxygen-porous electrode layers 16b, 16d provides an indication of $NO_x$ present in the gas.

As is the case with the embodiment of FIG. 2, a plurality of oxygen ion conductive ceramic layers are interposed between respective ones of the oxygen-porous electrode layers 16a, 16c and respective ones of the dissociative oxygen-porous electrode layers 16b, 16d. As will be appreciated by those practicing the present invention, an oxygen content electrical signal output is provided in the form of electrical leads coupled to the plurality of oxygen-porous electrode layers 16a, 16c. Similarly, a $NO_x$ content electrical signal output is provided in the form of electrical leads coupled to the plurality of dissociative oxygen-porous electrode layers 16b, 16d. In this manner, the oxygen-porous electrode layers 16a, 16c are coupled to an electrical signal output indicative of an oxygen content of gas within the diffusion-limited portion 218 of the gas passage 212 and the dissociative oxygen-porous electrode layers 16b, 16d are coupled to an electrical signal output indicative of an $NO_x$ content of gas within the diffusion-limited portion 218 of the gas passage 212.

The $NO_x$ content electrical signal output is electrically isolated from the oxygen content electrical signal output to ensure proper device performance. To further enhance device performance, the power source 30 and the electrode layers 16a, 16b, 16c, 16d are arranged such that the oxygen-porous electrode layer 16a and the dissociative oxygen-porous electrode layer 16b define the sole adjacent pair of different-type electrode layers and have matching polarity. The electrode layers 16a, 16b are also at substantially equivalent electrical potential (e.g., 0.1 VDC). In this manner, pumping of oxygen between the oxygen-porous electrode layer 16a and the dissociative oxygen-porous electrode layer 16b is inhibited. In contrast, the sensor arrangement illustrated in FIG. 2 includes electrode layers of alternating polarity.

At elevated temperatures, e.g., above about 600° C., Rh catalyzes the dissociation of $NO_x$ into $N_2$ and $O_2$. Accordingly, the dissociative oxygen-porous electrode layers 16b, 16d may comprise Rh. The non-dissociative electrode layers 16a, 16c may comprise oxygen porous platinum, as described above, and may additionally include Au in an amount sufficient to discourage catalysis of the dissociation of $NO_x$. As is noted above with reference to the oxygen sensor of FIG. 2, a heater or heating electrode is preferably configured to elevate the operating temperature of the combined sensor well above room temperature, typically in the vicinity of an operating temperature of about 800° C. The sensor is temperature independent in this range. The heater may, for example, be provided in the form of a heating electrode formed about the enclosure 210.

The partial enclosure 210 also defines an oxygen pumping portion 250 that is configured to maintain a favorable $NO_x$ to oxygen ratio in the diffusion limited portion 218 of the gas passage 212. Depending upon the operation constraints of the equipment used with the present invention, accurate measurement of $NO_x$ content may be problematic if the amount of oxygen in the diffusion limited portion relative to the amount of $NO_x$ is too high. The oxygen pumping portion 250 comprises an oxygen-porous cathode electrode 252, an oxygen-porous anode electrode 254, and an oxygen-ion conductive ceramic material 256. The oxygen-porous cathode electrode 252 is positioned over an interior surface of the partial enclosure 210 within the diffusion-limited portion 218 of the gas passage 212. The oxygen-porous anode electrode 254 is positioned over an exterior surface of the partial enclosure 210 outside of the diffusion-limited portion 218 of the gas passage 212. The oxygen-ion conductive ceramic material 256 is typically formed by the body of the enclosure 210 and, as such, is interposed between the cathode electrode 252 and the anode electrode 254. The oxygen-porous anode electrode 254 may comprise platinum and the oxygen-porous cathode electrode 252 may also comprise platinum with an amount of gold additive sufficient to discourage dissociation of $NO_x$.

Preferably, the $NO_x$ to oxygen ratio in the diffusion limited portion 218 is below about 5 parts oxygen to 1 part $NO_x$ but may be higher if the equipment used to measure amperometric current and control the voltages at the electrodes is optimized to account for higher oxygen levels. Accurate measurement of $NO_x$ content is problematic if the amount of oxygen in the diffusion limited portion relative to the amount of $NO_x$ is too high. For example, there is a logarithmically linear relationship between amperometric current and oxygen partial pressure below about 1000 ppm but accurate measurement is problematic above this level. A feedback loop may be coupled between the sensor body 220 and the oxygen pumping portion 250. The feedback loop may be configured to control the oxygen pumping portion 250 in response to the amount of oxygen sensed by the sensor body 220. Specifically, using the oxygen measurement from the sensor body 220, the rate of pumping oxygen out of the diffusion limited portion 218 can be continuously adjusted so that no more oxygen is pumped out of the tube interior than is needed to provide an accurate measurement of the $NO_x$ content (e.g., to keep the ratio of $NO_x$-released oxygen to background oxygen at, say, 1:5). The feedback loop may also be configured to switch the pumping function on and off in response to the amount of sensed oxygen. In this manner, operation of the oxygen pumping portion 250 may be operated to minimize power consumption of the combined sensor 200.

The oxygen sensor 240 is positioned in the inlet portion 214 of the gas passage 212 and provides a signal indicative of the oxygen partial pressure of the gas in the inlet portion 214. Thus, the combined sensor 200 is configured to provide independent indications of oxygen partial pressure and $NO_x$ content.

Turning now to the manner in which the $NO_x$ content is determined, $NO_x$ present in the gas within the diffusion limited portion 218 dissociates on the dissociative oxygen porous electrode layers 16b, 16d and the released oxygen creates an amperometric current at the $NO_x$ content electrical signal output. Oxygen in the surrounding gas also contributes to the $NO_x$ content electrical signal output, increasing the amperometric current because the dissociative electrodes 16b, 16d pump the oxygen in the gas and the oxygen dissociated from the $NO_x$ present in the gas. This "background" oxygen and the increased amperometric current can be accounted for using the oxygen content electrical signal output from the electrodes 16a, 16c because the corresponding amperometric current at the non-dissociative electrodes 16a, 16c provides an independent measure of the background oxygen.

As is noted above, to accurately measure the $NO_x$ content, it is also necessary to reduce the background oxygen in the diffusion limited portion to a level commensurate with the $NO_x$ released oxygen (e.g., to a ratio of about 5:1 (oxygen to $NO_x$).

As is noted above, the sensor body 220 has two separated sets of porous electrodes, one of which catalyzes the dissociation of $NO_x$ to nitrogen and oxygen. For convenience of illustration, FIG. 7 merely illustrates a pair of electrode layers in each set. However, it is contemplated that a large number of electrode layers could be provided in each set. Preferably, an equal number of electrode layers are provided in each set. However, it is contemplated by the present invention that more electrode layers could be provided in one set, relative to the other, as long as the difference in number is accounted for in the subsequent $NO_x$ content calculation.

The sensor 200 may be mounted directly in an exhaust or sample gas. There is no need for a reference gas supply. Particulate filters or other types of filters may be provided to prevent damage to the sensor and extend sensor life.

The sensor 200 is preferably manufactured in a manner similar to that discussed above with reference to the oxygen sensor of FIG. 2. Although a variety of manufacturing techniques are available, multi-layering manufacturing processes have the flexibility of producing layers electroded with Pt/Au and separate layers electroded with Rh in the same sensor body. Sensor leads are preferably embedded in the sensor body by drilling small holes (~0.5 mm) in the sensor body 220 in the green state. The sensor body 220 is then sintered and Pt wires are fired in the holes with a Pt paste. The stiffness of the Pt wires has the advantage of providing mechanical support. Leads for the oxygen sensor 240 are similarly embedded.

The length of the actual combined sensor may be about one inch (2.5 cm) and the major outside diameter may be about ½ inch (1.25 cm). The enclosure 210 may comprise a zirconia tube made by slip casting. The tube is typically milled in the green state to provide passageways for electrical leads and is subsequently sintered. The Pt/Au and Pt electrodes 252, 254 are then fired on the interior and exterior of the tube, respectively. Finally, using a commercial glass for sealing zirconia parts together, the sensor body 220, the diffusion barrier 230, and the oxygen sensor 240 are sealed in the zirconia tube in a single firing. The first two components are sealed hermetically. A Pt lead for the internal Pt/Au electrode passes through the wall of the tube and is also sealed hermetically. A slot in the zirconia tube at the large open end provides the passageway for two oxygen sensor leads, and opposing slots in the small closed end provide passageways for four dual-sensor leads. The sensor body or dual sensor 220 and its four leads are hermetically sealed in the zirconia tube with a commercially available glass.

Generally, the operation of the combined sensor 200 is as follows: The device is heated to, and maintained at, the operating temperature (e.g., 800° C.), and the oxygen sensor 240 measures the oxygen partial pressure of the exhaust or sample gas. The gas diffuses through the diffusion barrier 230 into the interior diffusion limited portion 218 of the enclosure or tube 210. A voltage applied across the cathode 252 and the anode 254 causes the oxygen in the interior to be pumped to a sufficiently low level. The sensor body 220 measures this low oxygen level with the non-dissociative layers 16a, 16c. The dissociative electrode layers 16b, 16d measure both the low oxygen level and the oxygen released from the NOx dissociation. These amperometric currents from both sets of electrodes are then used to determine the NOx content.

The zirconia diffusion barrier 230 diffusion-limits the amount of exhaust gas entering the interior of the tube and thereby ensures that a low level of oxygen can be reached in the interior by the pumping process (i.e., without this plug the interior would be constantly flooded with the exhaust gas). The NOx diffuses through this plug as molecular NOx.

The heater (not shown in FIG. 2) has a temperature-dependent resistance and thereby provides a means for measuring and controlling the operating temperature. A tradeoff is involved with the operating temperature, however: On the one hand, the higher the temperature, the more power is consumed by the heater in maintaining this temperature. On the other hand, the temperature should be high enough to reduce the resistance of the zirconia tube to a low value to avoid consuming large amounts of power in pumping the oxygen out of the tube interior.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to preferred embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A combined sensor for measuring oxygen content and $NO_x$ content in a gas, said sensor comprising;
    a partial enclosure defining a gas passage, an inlet portion, and an outlet portion;
    a diffusion barrier disposed between said inlet portion and said outlet portion, wherein said diffusion barrier defines a diffusion-limited portion of said gas passage on a side of said diffusion barrier opposite said inlet portion and a barrier between said diffusion-limited portion of said gas passage and said inlet portion of said gas passage;
    an oxygen sensor disposed in said inlet portion on a side of said diffusion barrier opposite said diffusion-limited portion of said gas passage, wherein said oxygen sensor is configured to provide a signal indicative of oxygen partial pressure in said inlet portion;
    a sensor body disposed in said partial enclosure on a side of said diffusion barrier opposite said inlet portion, wherein said sensor body comprises a plurality of non-dissociative oxygen-porous electrode layers and a plurality of dissociative oxygen-porous electrode layers, and said dissociative oxygen-porous electrode layers comprise a material selected to catalyze dissociation of $NO_x$ into nitrogen and oxygen;
    an oxygen content electrical signal output coupled to said plurality of non-dissociative oxygen-porous electrode layers for generating an indication of background oxygen within said diffusion limited portion of said gas passage; and
    a $NO_x$ content electrical signal output coupled to said plurality of dissociative oxygen-porous electrode layers.

2. A combined sensor for measuring oxygen content and $NO_x$ content in a gas as claimed in claim 1 wherein said gas passage defined by said partial enclosure defines an inlet portion and an outlet portion and wherein said sensor body extends across said outlet portion of said gas passage.

3. A combined sensor for measuring oxygen content and $NO_x$ content in a gas as claimed in claim 1 wherein at least a portion of said partial enclosure defines an oxygen pumping portion.

4. A combined sensor for measuring oxygen content and $NO_x$ content in a gas as claimed in claim 1 wherein at least a portion of said partial enclosure defines an oxygen pumping portion, said combined sensor further comprises a feedback loop coupled between said sensor body and said oxygen pumping portion, and said feedback loop is configured to control said oxygen pumping portion as a function of an amount of oxygen sensed by said sensor body.

5. A combined sensor for measuring oxygen content and $NO_x$ content in a gas as claimed in claim 4 wherein said feedback loop is configured to decrease a pump rate of said oxygen pumping portion as said amount of sensed oxygen decreases.

6. A combined sensor for measuring oxygen content and $NO_x$ content in a gas as claimed in claim 1 wherein at least a portion of said partial enclosure defines an oxygen pumping portion comprising:
    an oxygen-porous cathode electrode positioned over an interior surface of said partial enclosure within said diffusion-limited portion of said gas passage;
    an oxygen-porous anode electrode positioned over an exterior surface of said partial enclosure outside of said diffusion-limited portion of said gas passage; and
    an oxygen-ion conductive ceramic material interposed between said cathode electrode and said anode electrode.

7. A combined sensor for measuring oxygen content and $NO_x$ content in a gas as claimed in claim 6 wherein said oxygen-porous anode electrode comprises platinum and said oxygen-porous cathode electrode comprises platinum and gold.

8. A combined sensor for measuring oxygen content and $NO_x$ content in a gas as claimed in claim 1 wherein said plurality of oxygen-porous electrode layers comprise a material selected to inhibit dissociation of $NO_x$ into nitrogen and oxygen.

9. A combined sensor for measuring oxygen content and $NO_x$ content in a gas as claimed in claim 8 wherein said plurality of oxygen-porous electrode layers comprise Pt and Au.

10. A combined sensor for measuring oxygen content and $NO_x$ content in a gas as claimed in claim 1 wherein said plurality of plurality of dissociative oxygen-porous electrode layers comprise a material selected to catalyze dissociation of $NO_x$ into nitrogen and oxygen.

11. A combined sensor for measuring oxygen content and $NO_x$ content in a gas as claimed in claim 10 wherein said dissociative oxygen-porous electrode layer material is selected to catalyze dissociation of $NO_x$ into $N_2$ and $O_2$.

12. A combined sensor for measuring oxygen cement and $NO_x$ content in a gas as claimed in claim 11 wherein said plurality of dissociative oxygen-porous electrode layers comprise sufficient Rh to catalyze dissociation of NOX into nitrogen and oxygen.

13. A combined sensor for measuring oxygen content and $NO_x$ content in a gas as claimed in claim 1 wherein said combined sensor further comprises a power source, said power source is configured such that an oxygen-porous electrode layer and a dissociative oxygen-porous electrode layer define respective ones of an adjacent pair of electrode layers having matching polarity and substantially equivalent electrical potential such that pumping of oxygen between said oxygen-porous electrode layer and a dissociative oxygen-porous electrode layer is inhibited.

14. A combined sensor for measuring oxygen content and $NO_x$ content in a gas as claimed in claim 1 wherein said oxygen-porous electrode layers are electrically isolated from said dissociative oxygen-porous electrode layers.

15. A combined sensor for measuring oxygen content and $NO_x$ content in a gas as claimed in claim 1 wherein said plurality of oxygen-porous electrode layers are coupled to an electrical signal output that is independent of an electrical signal output to which said dissociative oxygen-porous electrode layers are coupled.

16. A combined sensor for measuring oxygen content and $NO_x$ content in a gas as claimed in claim 15 wherein said oxygen-porous electrode layers are coupled to an electrical signal output indicative of an oxygen content of gas within said diffusion-limited portion of said gas passage and said dissociative oxygen-porous electrode layers are coupled to an electrical signal output indicative of an $NO_x$ content of gas within said diffusion-limited portion of said gas passage.

17. A combined sensor for measuring oxygen content and $NO_x$ content in a gas as claimed in claim 1 wherein said partial enclosure comprises an oxygen-ion conductive ceramic tube and said diffusion barrier extends across an inside diameter of said tube defining a barrier between said diffusion-limited portion of said gas passage and an inlet portion of said gas passage.

18. A combined sensor for measuring oxygen content and $NO_x$ content in a gas as claimed in claim 1 wherein said diffusion-limited portion of said gas passage comprises a hermetically sealed zone including a diffusion inlet defined by said diffusion barrier ad a sensor outlet defined by said sensor body.

19. A combined sensor for measuring oxygen content and $NO_x$ content in a gas as claimed in claim 18 wherein said hermetically sealed zone further comprises an oxygen pumping portion.

20. A combined sensor for measuring oxygen content ad $NO_x$ content in a gas as claimed in claim 1 wherein said diffusion barrier comprises a zirconia partition.

21. A combined sensor for measuring oxygen content and $NO_x$ content in a gas as claimed in claim 1 wherein said diffusion barrier extends across said gas passage.

22. A combined sensor for measuring oxygen content and $NO_x$ content in a gas as claimed in claim 21 wherein said diffusion barrier comprises a substantially uniform partition.

23. A combined sensor for measuring oxygen content and $NO_x$ content in a gas as claimed in claim 1 wherein said diffusion barrier is configured to pass an amount of gas that varies as a function of oxygen partial pressure of gas within an inlet portion of said gas passage.

24. A combined sensor for measuring oxygen content and $NO_x$ content in a gas as claimed in claim 1 further comprising a heater configured to elevate an operating temperature of said combined sensor to about 800° C.

25. A combined sensor for measuring oxygen content and $NO_x$ content in a gas as claimed in claim 24 wherein said partial enclosure comprises a zirconia tube and said heater is formed about said zirconia enclosure.

26. A combined sensor for measuring oxygen content and $NO_x$ content in a gas as claimed in claim 1 wherein said sensor body further comprises a plurality of oxygen ion conductive ceramic layers interposed between respective ones of said oxygen-porous electrode layers and respective ones of said dissociative oxygen-porous electrode layers.

27. A combined sensor for measuring oxygen content and NOX content in a gas, said sensor comprising:

a partial enclosure defining a gas passage, an inlet portion, and an outlet portion;

a diffusion barrier disposed between said inlet portion and said outlet portion;

a monolithic sensor body disposed in said partial enclosure on a side of said diffusion barrier opposite said inlet portion, wherein said sensor body comprises a plurality of non-dissociative oxygen-porous electrode layers interdispersed between ceramic layers of said monolithic sensor body and a plurality of dissociative oxygen-porous electrode layers interdispersed between ceramic layers of said monolithic sensor body, said electrode and said ceramic layers being arranged to form a monolithic sensor body having alternating ceramic and metallic layers;

an oxygen content electrical signal output coupled to said plurality of non-dissociative oxygen-porous electrode layers for generating an indication of background oxygen within said diffusion limited portion of said gas passage; and a NOX content electrical signal output coupled to said plurality of dissociative oxygen-porous electrode layers.

28. A combined sensor for measuring oxygen content and $NO_x$ content in a gas as claimed in claim 27, wherein said electrode layers are arranged such that one of said non-dissociative electrode layers and one of said dissociative electrode layers define the sole adjacent pair of different-type electrode layers of said monolithic sensor body and have matching polarity.

* * * * *

UNITED STATES PATENT AND TRADEMARK OFFICE
CERTIFICATE OF CORRECTION

PATENT NO. : 6,824,661 B2
DATED : November 30, 2004
INVENTOR(S) : William N. Lawless It is certified that error appears in the above-identified patent and that said Letters Patent is hereby corrected as shown below:

Column 6,
Lines 45-46, "oxygen partial pressures. An" should read -- oxygen partial pressures. An --

Column 14,
Line 49, "cement" should read -- content --

Column 15,
Line 26, "ad a" should read -- and a --

Signed and Sealed this

Thirty-first Day of May, 2005

JON W. DUDAS
*Director of the United States Patent and Trademark Office*